US 9,155,579 B2

(12) United States Patent
Konieczynski et al.

(10) Patent No.: US 9,155,579 B2
(45) Date of Patent: *Oct. 13, 2015

(54) POLYAXIAL BONE SCREW

(71) Applicant: DePuy Synthes Products, Inc., Raynham, MA (US)

(72) Inventors: David D. Konieczynski, Needham, MA (US); Thomas V. Doherty, Irvine, CA (US); Dale E. Whipple, Ackworth, GA (US); Niall Casey, San Diego, CA (US); Mark T. Hall, Bridgewater, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/157,081

(22) Filed: Jan. 16, 2014

(65) Prior Publication Data

US 2014/0180347 A1     Jun. 26, 2014

Related U.S. Application Data

(63) Continuation of application No. 13/657,486, filed on Oct. 22, 2012, now Pat. No. 8,663,288, which is a continuation of application No. 12/698,612, filed on Feb. 2, 2010, now Pat. No. 8,313,516, which is a (Continued)

(51) Int. Cl.
*A61B 17/86* (2006.01)
*A61B 17/70* (2006.01)

(52) U.S. Cl.
CPC ......... *A61B 17/8605* (2013.01); *A61B 17/7037* (2013.01); *A61B 17/7032* (2013.01); *A61B 17/7035* (2013.01)

(58) Field of Classification Search
CPC .......... A61B 17/8605; A61B 17/7037; A61B 17/7035
USPC .............. 606/266, 269, 305–308; 403/90, 93, 403/132, 144, 56, 140, 138; 411/340–346
See application file for complete search history.

(56) References Cited

U.S. PATENT DOCUMENTS

| 2,992,669 A | 7/1961 | Fesmire |
| 4,411,259 A | 10/1983 | Drummond |

(Continued)

FOREIGN PATENT DOCUMENTS

| EP | 0 128 058 A1 | 12/1984 |
| EP | 1169971 A2 | 1/2002 |

(Continued)

OTHER PUBLICATIONS

DePuy Spine, "Speed Security and Simplicity in Harmony, Expedium Spine System," 6 pages, Aug. 2004.

(Continued)

*Primary Examiner* — Andrew Yang
(74) *Attorney, Agent, or Firm* — Nutter McClennen & Fish LLP

(57) ABSTRACT

The present invention generally provides a polyaxial fixation device having a shank with a spherical head formed on a proximal end thereof, and a receiver member having an axial passage formed therein that is adapted to polyaxially seat the spherical head of the shank. The polyaxial bone screw further includes an engagement member that is adapted to provide sufficient friction between the spherical head and the receiver member to enable the shank to be maintained in a desired angular orientation before locking the spherical head within the receiver member.

9 Claims, 11 Drawing Sheets

Related U.S. Application Data continuation of application No. 11/381,048, filed on May 1, 2006, now Pat. No. 7,682,377, which is a continuation of application No. 10/608,904, filed on Jun. 27, 2003, now Pat. No. 7,087,057.

(56) References Cited

U.S. PATENT DOCUMENTS

| | | |
|---|---|---|
| 5,005,562 A | 4/1991 | Cotrel |
| 5,135,489 A | 8/1992 | Jepson et al. |
| 5,207,678 A | 5/1993 | Harms et al. |
| 5,443,467 A | 8/1995 | Biedermann et al. |
| 5,466,237 A | 11/1995 | Byrd, III et al. |
| 5,474,555 A | 12/1995 | Puno et al. |
| 5,476,464 A | 12/1995 | Metz-Stavenhagen et al. |
| 5,613,968 A | 3/1997 | Lin |
| 5,639,074 A | 6/1997 | Greenhill et al. |
| 5,669,911 A | 9/1997 | Errico et al. |
| 5,672,176 A | 9/1997 | Biedermann et al. |
| 5,690,630 A | 11/1997 | Errico et al. |
| 5,733,285 A | 3/1998 | Errico et al. |
| 5,797,911 A | 8/1998 | Sherman et al. |
| 5,817,094 A | 10/1998 | Errico et al. |
| 5,876,402 A | 3/1999 | Errico et al. |
| 5,879,350 A | 3/1999 | Sherman et al. |
| 5,885,286 A | 3/1999 | Sherman et al. |
| 5,964,760 A | 10/1999 | Richelsoph |
| 6,010,503 A | 1/2000 | Richelsoph et al. |
| 6,022,350 A | 2/2000 | Ganem |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,090,110 A | 7/2000 | Metz-Stavenhagen |
| 6,090,111 A | 7/2000 | Nichols |
| 6,113,601 A | 9/2000 | Tatar |
| 6,139,550 A | 10/2000 | Michelson |
| 6,238,396 B1 | 5/2001 | Lombardo |
| 6,261,287 B1 | 7/2001 | Metz-Stavenhagen |
| 6,261,291 B1 | 7/2001 | Talaber et al. |
| 6,280,442 B1 | 8/2001 | Barker et al. |
| 6,287,311 B1 | 9/2001 | Sherman et al. |
| 6,296,642 B1 | 10/2001 | Morrison et al. |
| 6,302,888 B1 | 10/2001 | Mellinger et al. |
| 6,375,657 B1 | 4/2002 | Doubler et al. |
| 6,402,752 B2 | 6/2002 | Schaffler-Wachter et al. |
| 6,440,137 B1 | 8/2002 | Horvath et al. |
| 6,454,768 B1 | 9/2002 | Jackson |
| 6,471,705 B1 | 10/2002 | Biedermann et al. |
| 6,485,491 B1 | 11/2002 | Farris et al. |
| 6,488,681 B2 | 12/2002 | Martin et al. |
| 6,511,099 B2 | 1/2003 | Bartholoma et al. |
| 6,520,963 B1 | 2/2003 | McKinley |
| 6,530,929 B1 | 3/2003 | Justis et al. |
| 6,537,276 B2 | 3/2003 | Metz-Stavenhagen |
| 6,540,748 B2 | 4/2003 | Lombardo |
| 6,547,725 B1 | 4/2003 | Paolitto et al. |
| 6,551,323 B2 | 4/2003 | Doubler et al. |
| 6,565,565 B1 | 5/2003 | Yuan et al. |
| 6,565,567 B1 | 5/2003 | Haider |
| 6,585,740 B2 | 7/2003 | Schlapfer et al. |
| 6,660,004 B2 | 12/2003 | Barker et al. |
| 6,726,687 B2 | 4/2004 | Jackson |
| 6,740,086 B2 | 5/2004 | Richelsoph |
| 6,755,829 B1 | 6/2004 | Bono et al. |
| 6,835,196 B2 | 12/2004 | Biedermann et al. |
| 6,837,889 B2 | 1/2005 | Shluzas |
| 6,869,433 B2 | 3/2005 | Glascott |
| 6,905,500 B2 | 6/2005 | Jeon et al. |
| 7,018,378 B2 | 3/2006 | Biedermann et al. |
| 7,066,937 B2 | 6/2006 | Shluzas |
| 7,087,057 B2 | 8/2006 | Konieczynski et al. |
| 7,144,396 B2 | 12/2006 | Shluzas |
| 7,682,377 B2 | 3/2010 | Konieczynski et al. |
| 7,686,834 B2 | 3/2010 | Saint Martin |
| 8,313,516 B2 | 11/2012 | Konieczynski et al. |
| 8,663,288 B2 | 3/2014 | Konieczynski et al. |
| 2001/0001119 A1 | 5/2001 | Lombardo |
| 2002/0026193 A1 | 2/2002 | Barker et al. |
| 2002/0058942 A1 | 5/2002 | Biedermann et al. |
| 2002/0091386 A1 | 7/2002 | Martin et al. |
| 2002/0138076 A1 | 9/2002 | Biedermann et al. |
| 2003/0004512 A1 | 1/2003 | Farris et al. |
| 2003/0032957 A1 | 2/2003 | McKinley |
| 2003/0055426 A1 | 3/2003 | Carbone et al. |
| 2003/0153911 A1 | 8/2003 | Shluzas |
| 2003/0167058 A1 | 9/2003 | Shluzas |
| 2004/0153068 A1 | 8/2004 | Janowski et al. |
| 2004/0176766 A1 | 9/2004 | Shluzas |
| 2004/0267264 A1 | 12/2004 | Konieczynski et al. |
| 2006/0241599 A1 | 10/2006 | Konieczynski et al. |
| 2006/0276791 A1 | 12/2006 | Shluzas |
| 2006/0293665 A1 | 12/2006 | Shluzas |
| 2008/0140135 A1 | 6/2008 | Konieczynski et al. |
| 2010/0131018 A1 | 5/2010 | Konieczynski et al. |
| 2013/0103099 A1 | 4/2013 | Konieczynski et al. |

FOREIGN PATENT DOCUMENTS

| | | |
|---|---|---|
| EP | 1474050 A1 | 11/2004 |
| GB | 812248 A | 4/1959 |
| WO | 9965415 A1 | 12/1999 |
| WO | 02/22030 | 3/2002 |
| WO | 03/037199 A1 | 5/2003 |
| WO | 03/068083 A1 | 8/2003 |
| WO | 11005612 A2 | 1/2011 |

OTHER PUBLICATIONS

International Search Report for PCT/US04/18602 mailed Sep. 15, 2005.

Written Opinion for PCT/US04/18602 mailed Dec. 27, 2005.

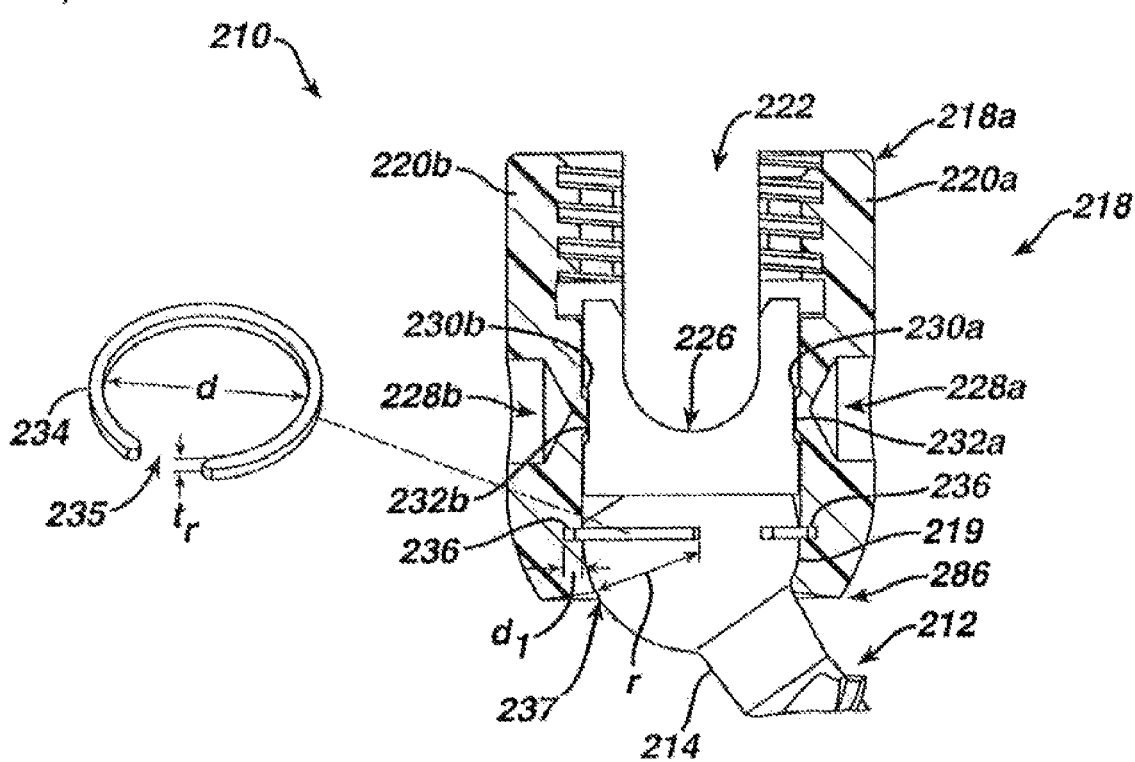

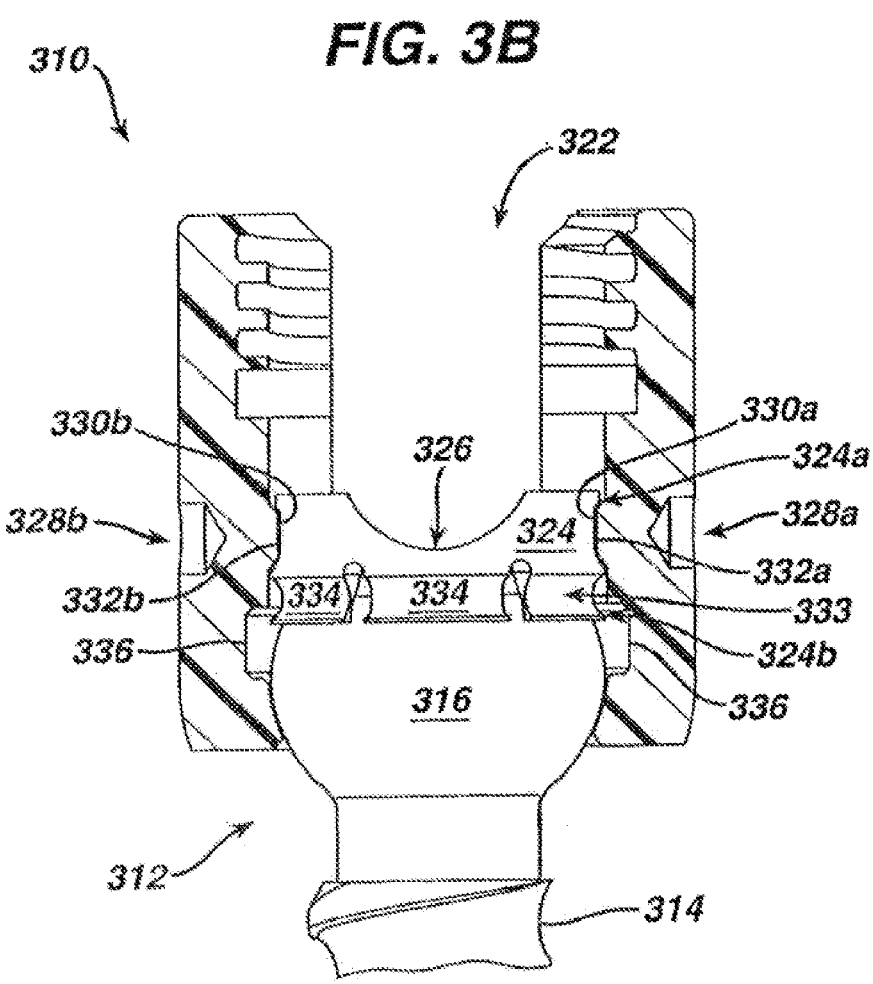

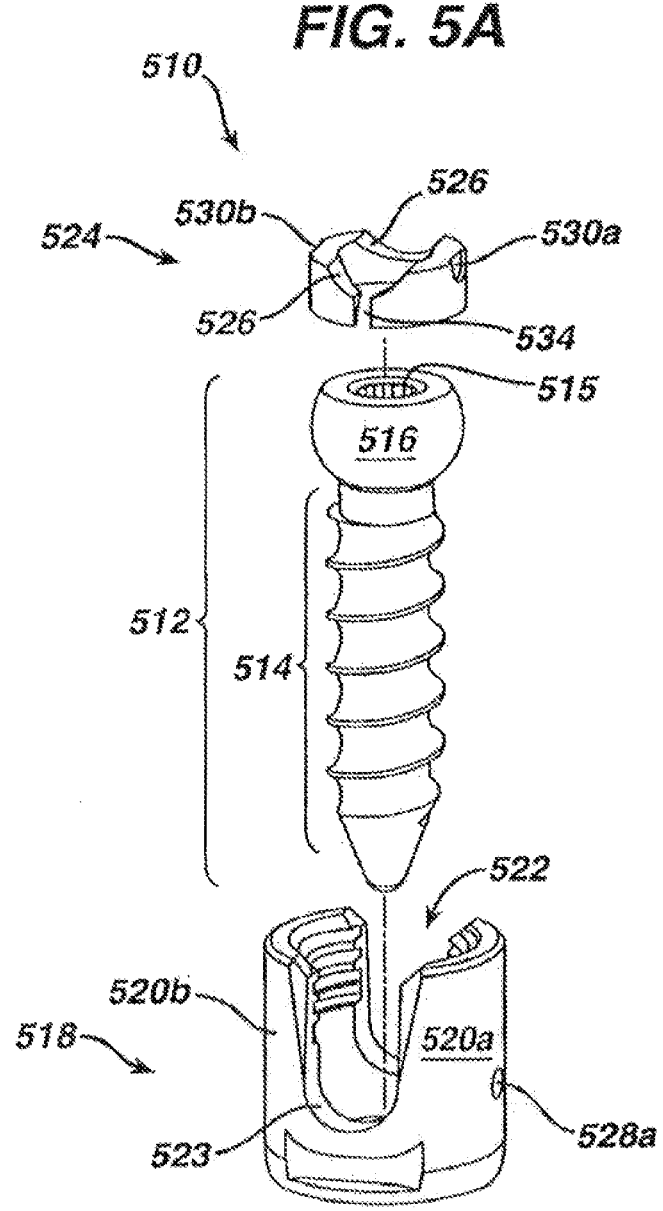

POLYAXIAL BONE SCREW

CROSS REFERENCE TO RELATED APPLICATIONS

The present application is a continuation of U.S. application Ser. No. 13/657,486, filed on Oct. 22, 2012 entitled "Polyaxial Bone Screw," which is a continuation of U.S. patent application Ser. No. 12/698,612 (now U.S. Pat. No. 8,313,516) filed on Feb. 2, 2010 and entitled "Polyaxial Bone Screw," which is a continuation of U.S. patent application Ser. No. 11/381,048 (now U.S. Pat. No. 7,682,377) filed on May 1, 2006 and entitled "Polyaxial Bone Screw," which is a continuation of U.S. patent application Ser. No. 10/608,904 (now U.S. Pat. No. 7,087,057) filed on Jun. 27, 2003 and entitled "Polyaxial Bone Screw," which are hereby incorporated by reference in their entireties.

FIELD OF THE INVENTION

The present invention relates to polyaxial bone screws, and in particular to a polyaxial bone screw assembly in which the bone screw can be maintained in a desired angular orientation prior to locking the bone screw with respect to the rod-receiving member.

BACKGROUND OF THE INVENTION

Spinal fixation devices are used in orthopedic surgery to align and/or fix a desired relationship between adjacent vertebral bodies. Such devices typically include a spinal fixation element, such as a relatively rigid fixation rod, that is coupled to adjacent vertebrae by attaching the element to various anchoring devices, such as hooks, bolts, wires, or screws. The fixation rods can have a predetermined contour that has been designed according to the properties of the target implantation site, and once installed, the instrument holds the vertebrae in a desired spatial relationship, either until desired healing or spinal fusion has taken place, or for some longer period of time.

Spinal fixation devices can be anchored to specific portions of the vertebra. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a bone screw with a threaded shank that is adapted to be threaded into a vertebra, and a rod-receiving element, usually in the form of a U-shaped slot formed in the head. The shank and rod-receiving assembly can be provided as a monoaxial screw, whereby the rod-receiving element is fixed with respect to the shank, or a polyaxial screw, whereby the rod-receiving element has free angular movement with respect to the shank. In use, the shank portion of each screw is threaded into a vertebra, and once properly positioned, a fixation rod is seated into the rod-receiving element of each screw. The rod is then locked in place by tightening a set-screw, plug, or similar type of fastening mechanism into the rod-receiving element.

While current spinal fixation systems have proven effective, it can be difficult to mount rods into the rod-receiving element of various fixation devices. In particular, it can be difficult to align and seat a rod into the rod-receiver of a polyaxial implant since the rod-receiver has polyaxial freedom of movement with respect to the shank. More particularly, the polyaxial freedom of movement of the rod-receiver can allow the receiver to "flop," thereby requiring the surgeon or an assistant to hold the receiver in the desired position during rod introduction.

Accordingly, there remains a need for a polyaxial bone screw assembly in which the rod-receiving element can be maintained in a desired angular orientation before locking the shank with respect to the receiver member.

SUMMARY OF THE INVENTION

The present invention generally provides a polyaxial spinal fixation device (e.g., bone screws, hooks, etc.) having a shank with a spherical head formed on a proximal end thereof, and a receiver member having an axial passage formed therein that is adapted to polyaxially seat the spherical head of the shank. The polyaxial fixation device further includes an engagement member that is adapted to provide sufficient friction between the spherical head and the receiver member to enable the shank to be maintained in a desired angular orientation before locking the spherical head within the receiver member. The engagement member can have a variety of configurations, and in one embodiment the engagement member can be a ring member, such as a snap ring, that is positioned to engage a portion of the spherical head to provide frictional engagement between the head and the receiver member. The ring member can be disposed within a groove formed around an outer surface of the spherical head of the shank, and/or it can be disposed within a groove formed around an inner surface of the receiver member. The groove around the inner surface of the receiver member preferably has a depth that is equal to or greater than a thickness of the ring member to allow the ring member to be completely disposed within the groove. Alternatively, or in addition, the ring member can be adapted to expand or contract to be disposed completely within the groove.

In another embodiment, the engagement member can be a compression cap that is disposed within the receiver member and that has a concave distal surface adapted to seat at least a portion of the spherical head of the shank. The compression cap is preferably capable of mating with the receiver member such that the compression cap is effective to retain the spherical head of the shank in a spherical recess formed in the receiver member. The compression cap can have a variety of configurations, and in one embodiment it can include opposed leaf-spring members that are adapted to contract inward, biasing the cap distally, to frictionally engage the spherical head of the shank. In another embodiment, at least a portion of the compression cap has a diameter that is expandable to frictionally engage the spherical head. By way of non-limiting example, the compression cap can include a plurality of distally-extending finger-like members formed around a distal edge of the compression cap to frictionally engage the spherical head. In yet another embodiment, the compression cap can include at least one longitudinally oriented slot formed therein to allow the compression cap to be contracted to frictionally engage the spherical head.

In other aspects, a polyaxial fixation assembly is provided having a shank with a spherical head formed on a proximal end thereof, and a receiver member having a first, proximal opening adapted to receive a spinal fixation rod and a second, distal opening having a diameter sized to permit passage of the shank therethrough while maintaining the spherical head therein. The receiver member further includes a spherical seat adjacent the second, distal opening to polyaxially seat the spherical head of the shank. The polyaxial fixation assembly also includes means for frictionally engaging the spherical head to maintain the shank in a desired angular orientation such that a force greater than a frictional engagement force is required to change the angular orientation of the threaded shank with respect to the receiver member.

BRIEF DESCRIPTION OF THE DRAWINGS

The invention will be more fully understood from the following detailed description taken in conjunction with the accompanying drawings, in which:

FIG. 2A is an enlarged, partially cross-sectional view of a polyaxial bone screw assembly having a ring member disposed therein in accordance with one embodiment of the present invention;

FIG. 3B is an enlarged, partially cross-sectional view of a portion of the polyaxial bone screw assembly shown in FIG. 3A;

FIG. 5A is a perspective view of yet another embodiment of a polyaxial bone screw assembly, in the disassembled state, having a compression cap with a slot formed therein to allow the compression cap to engage the head of a bone screw in accordance with the present invention.

DETAILED DESCRIPTION OF THE INVENTION

Figure 1:
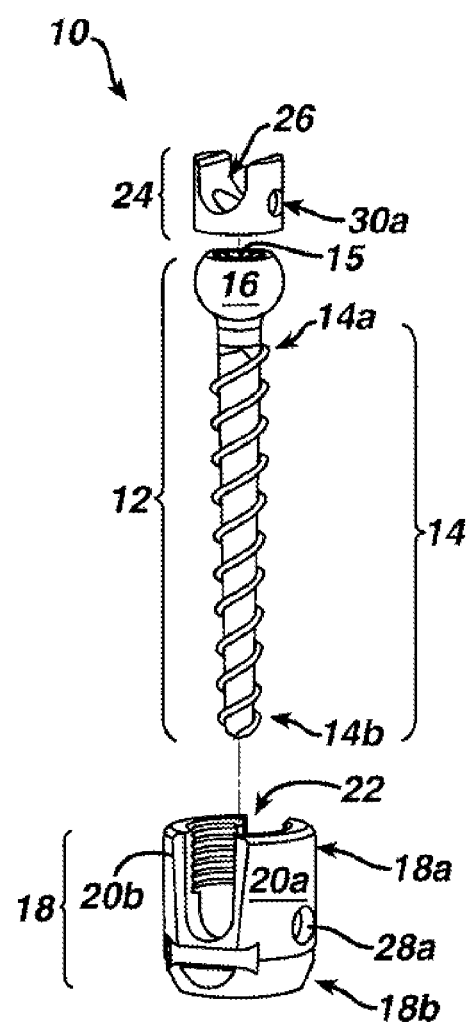
FIG. 1 is a perspective view of a prior art polyaxial bone screw.

FIG. 1 illustrates a prior art polyaxial bone screw assembly 10 that includes a bone screw 12, a receiver member 18, and a compression cap 24. As shown, the bone screw 12 generally includes a threaded shank 14 having a spherical head 16 formed on a proximal end 14a thereof. An Allen or other female socket 15 is formed in the head 16 for applying torque along the axis of the shank 14 to insert the shank 14 into bone. The receiver member 18 is generally U-shaped and includes opposed side walls or legs 20a, 20b that are substantially parallel to one another and that define a rod-receiving portion 22 for seating a spinal fixation rod. A distal end 18b of the receiver member 18 includes an axial opening (not shown) formed therein and having a diameter sized to permit passage of the shank 14 therethrough while maintaining the spherical head 16 therein. The receiver member 18 further includes a spherical seat (not shown) adjacent to the distal opening for polyaxially seating the spherical head 16 of the bone screw 12. The compression cap 24, which is adapted to be positioned within the receiver member 18, has a generally cylindrical shape and includes a rod-receiving proximal surface 26, and a concave distal surface (not shown) that is adapted to fit around and seat a portion of the spherical head 16 of the bone screw 12.

In use, the threaded shank 14 is disposed through the distal opening in the receiver member 18 and the spherical head 16 of the bone screw 12 is positioned within the spherical seat in the receiver member 18. The compression cap 24 is then inserted into the receiver member 18 such that the concave distal surface of the compression cap 24 is disposed around and seats a portion of the spherical head 16 of the bone screw 12. In order to retain the compression cap 24 within the receiver member 18, the receiver member 18 includes opposed sides bores (only one side bore 28a is shown) having a deformable material (not shown) extending there across on an inner surface of the receiver member 18. The side bores 28a allow the material to be deformed inward to extend into and engage opposed detents (only one detent 30a is shown) formed in the compression cap 24. A tool can be used to deform the material into the detents 30a once the compression cap 24 is disposed within the receiver 18. As a result, the compression cap 24 is maintained within the receiver member 18, thereby preventing removal of the bone screw 12 from the receiver member 18. The compression cap 24 is also effective to lock the bone screw 12 in a desired angular orientation with respect to the receiver member 18 once a rod is disposed and locked within the receiver member 18. A person skilled in the art will appreciate that a variety of techniques can be used to retain the compression cap 24 within the receiver member 18, and that the present invention is not intended to be limited to use with compression caps 24 having detents for receiving deformable material disposed within the receiver member. By way of non-limiting example, the compression cap 24 can be retained within the receiver 18 using a cross-pin.

Once the bone screw 12 is implanted within bone, and prior to insertion of a rod into the receiver member 18, the receiver member 18 of the prior art assembly is free to rotate and/or be angularly positioned with respect to the bone screw 12. While this advantageously allows alignment of the receiver member 18 with a rod adapted to be disposed therein, such free axial movement of the receiver member 18 can present challenges during surgery as the surgeon is required to hold the receiver member 18 in the desired position during rod introduction.

Accordingly, the present invention provides mechanisms for creating friction between the spherical head 16 and the receiver member 18 to allow the receiver member 18 to be provisionally maintained in a desired angular orientation prior to locking the receiver member 18 with respect to the a polyaxial fixation device. This is particularly advantageous in that it allows a surgeon to position and maintain the receiver member 18 in a desired orientation prior to rod introduction, thereby preventing the receiver member 18 from moving with respect to the bone screw 12 during introduction of a rod. While several different techniques can be used to create the necessary frictional forces to allow the angular orientation between the receiver member 18 and the bone screw 12 to be maintained, FIGS. 2A-5B illustrate several exemplary embodiments for frictionally engaging the spherical head of a bone screw with respect to a rod-receiver member. For convenience purposes, the reference numbers used in the embodiments shown in FIGS. 2A-5B correspond to the reference numbers used in FIG. 1, except that a different prefix is added to the reference numbers for each embodiment. A person skilled in the art will appreciate that a variety of other techniques can be used to create the frictional forces necessary to maintain the angular orientation of the shank with respect to the receiver member. Moreover, the techniques used to create friction between the spherical head and the receiver member can be adapted for use with virtually any polyaxial spinal fixation device in addition to the illustrated bone screw assembly, and the invention is not intended to be limited to the specific polyaxial bone screw assembly shown.

Figure 2B:
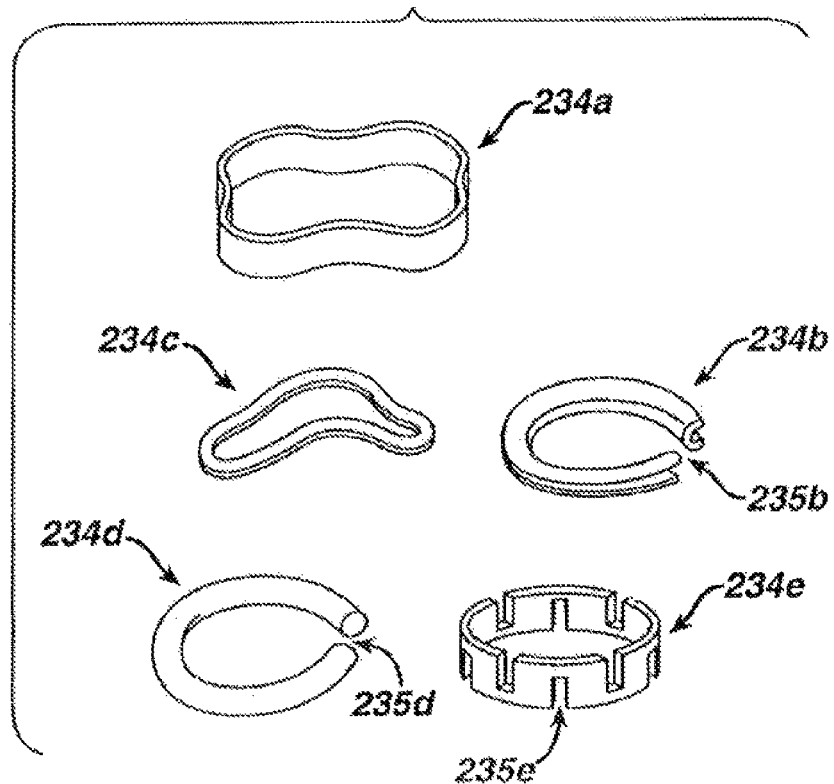
FIG. 2B illustrates several embodiments of a ring member that can be used with the polyaxial bone screw assembly shown in FIG. 2A.

FIG. 2A illustrates one embodiment of a polyaxial bone screw assembly 210 that utilizes a ring member, e.g., a snap ring 234, to frictionally engage the spherical head 216 of the bone screw 212. The snap ring 234 can have a variety of configurations, shapes, and sizes, but it should be adapted to expand to fit around at least a portion of the spherical head 216. As shown, the snap ring 234 is in the shape of a loop with an opening 235 formed therein that allows the diameter d of the snap ring 234 to expand to fit around a portion of the spherical head 216 of the bone screw 212. While the snap ring 234 is shown having a C-shape, the snap ring can 234 can have a variety of other configurations. By way of non-limiting example, FIG. 2B illustrates a variety of different snap rings 234a, 234b, 234c, 234d, 234e that can be used with the polyaxial bone screw assembly 210 shown in FIG. 2A. Snap rings 234a and 234c, for example, each have an irregular shape that allows the snap rings 234a, 234c to expand to fit around the spherical head 216 of the bone screw 212. Snap ring 234e, on the other hand, includes several cut-out portions 235e that allow the snap ring 234e to expand. In other embodiments, the snap ring 234 can have a variety of different cross-sectional shapes such as, for example, a circular cross-sectional shape as shown on snap ring 234d, or a C-shaped cross-section as shown on snap ring 234b.

While the snap ring 234 can have a variety of configurations, the snap ring 234 should be adapted to fit within a corresponding groove 236 formed around an inner surface of the receiver member 218. The groove 236 maintains the snap ring 234 at a particular location with respect to the spherical head 216 of the bone screw such that the snap ring 234 is expanded around the head 216. More particularly, the groove 236 should be formed in a proximal portion of the spherical seat 219 formed in the distal end 218b of the receiver member 218. Not only is the groove 236 effective to maintain the position of the snap ring 234 around the spherical head 216, but it is also effective to fully seat the snap ring 234 when the head 216 is locked within the receiver 218. As previously discussed, when a rod is seated within the receiver member 218, the compression cap 224 is forced distally to lock the bone screw 216 with respect to the receiver 218. The groove 236 receives the snap ring 234 to prevent the snap ring 234 from interfering with the locking function of the compression cap 224. Accordingly, the groove 236 preferably has a depth $d_1$ that is at least equal to, and more preferably is greater than, a thickness $t_r$ of the snap ring 234. Alternatively, or in addition, the snap ring 234 can be adapted to expand or contract to be completely disposed within the groove 236. By way of non-limiting example, the snap ring 234 can be formed from a compressible or deformable material that allows the snap ring 234 to be forced completely into the groove 236.

Still referring to FIG. 2A, the bone screw assembly 210 can be assembled by first placing the snap ring 234 within the groove 236 in the receiver member 218. The threaded shank 214 of the screw 212 can then be inserted through the axial opening 237 formed in the distal end 218b of the receiver member 218. As a result, the spherical head 216 will rest on top of the snap ring 234. The compression cap 224 can then be placed in the receiver 218 and can be used to push the head 216 into the recess 219, thereby causing the snap ring 234 to expand around the head 216 to engage the head 216. This can be achieved by using a tool to push the compression cap 224 in a distal direction. To prevent the compression cap 224 from popping out of the receiver 218, another tool can be inserted into each of the opposed bores 228a, 228b to deform the deformable material 232a, 232b, which extends across the inner surface of the receiver member 218, into the corresponding detents 230a, 230b formed in the compression cap 224. As a result, the compression cap 224 is prevented from moving in a proximal direction, thereby preventing the spherical head 216 from moving proximally and becoming disengaged with the snap ring 234. One skilled in the art will appreciate that a variety of other techniques and fastening members are known for use in retaining the spherical head 216 (and any rod) within the receiver 218.

Once the device 210 is assembled, the frictional forces created by the snap ring 234 that act on the spherical head 216 of the screw 212 will allow the screw 212 to be set at a desired angular orientation with respect to the receiver member 218, as shown in FIG. 2A. The frictional forces can simply be overcome by grasping and moving the bone screw 212 with respect to the receiver member 218 to change the angular orientation. In other words, a force greater than the frictional engagement force is required to change the angular orientation of the bone screw 212 with respect to the receiver member 218.

Figure 2C:
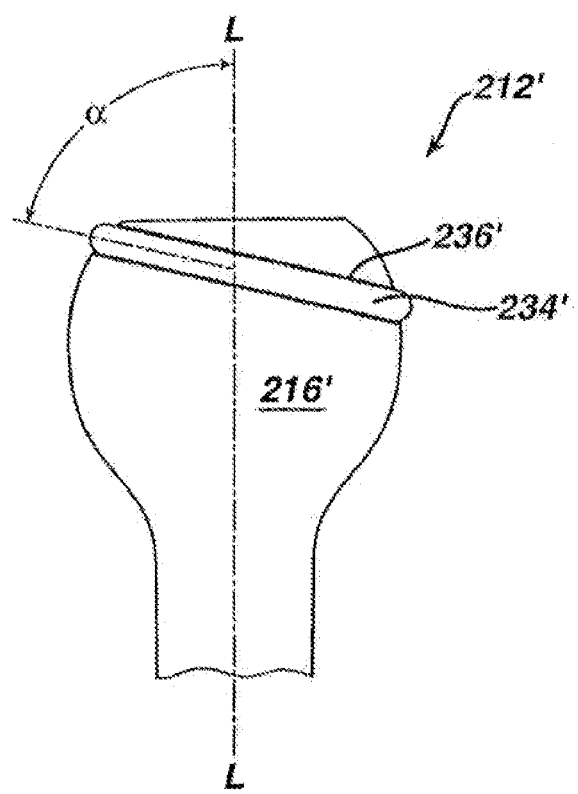
FIG. 2C is an illustration of another embodiment of a bone screw having a ring member disposed therearound.

In another embodiment, shown in FIG. 2C, the snap ring 234 can be disposed within a groove 236' formed around the spherical head 216' of the bone screw 212', rather than in a groove 236 formed within the receiver member 218. In this embodiment, the groove 236' around the head 216' of the bone screw 212' preferably extends at an angle a, with respect to a longitudinal axis L of the screw 212', around the proximal half of the spherical head 216' to allow the head 216' to fit within the spherical recess 219 in the receiver member 218. The angle α of the groove 236' also allows the snap ring 234 to bear against the concave inner surface of the compression cap 224, thereby creating the necessary frictional forces to allow the angular orientation of the bone screw 212' to be maintained with respect to the receiver member 218.

Figure 3A:
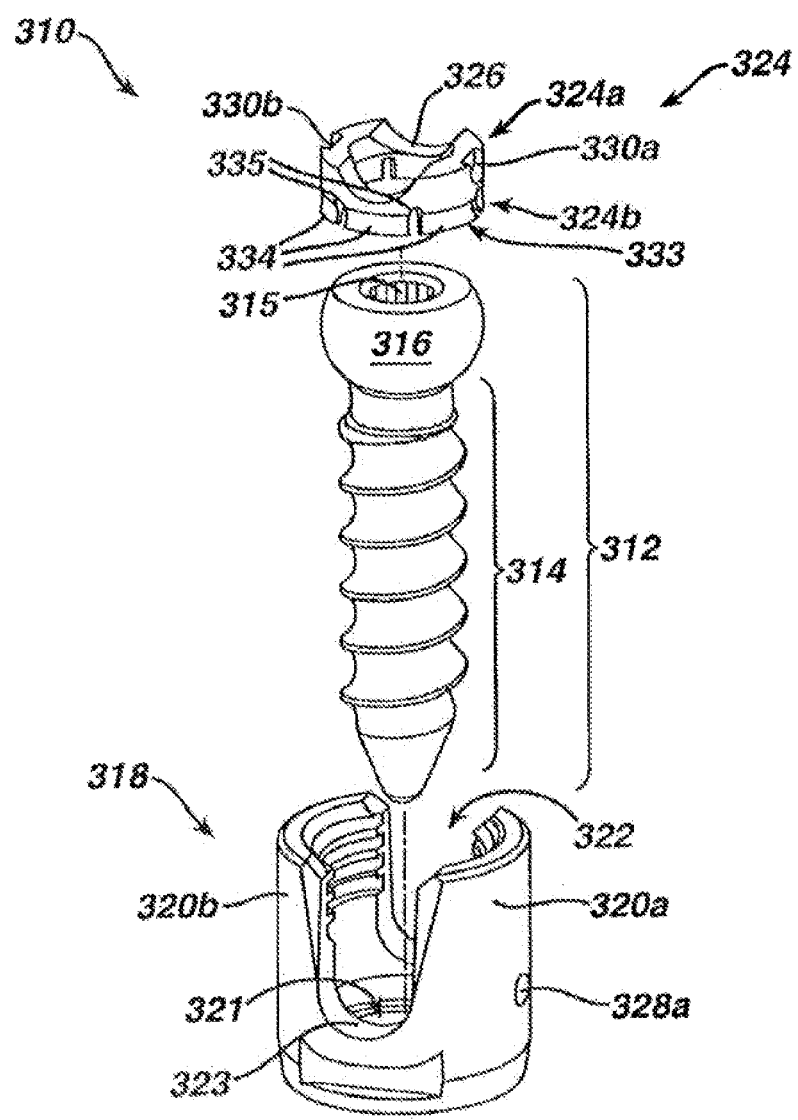
FIG. 3A is a perspective view of a polyaxial bone screw assembly, in the disassembled state, having a compression cap with a collet for engaging the head of a bone screw in accordance with another embodiment of the present invention.
Figure 3C:
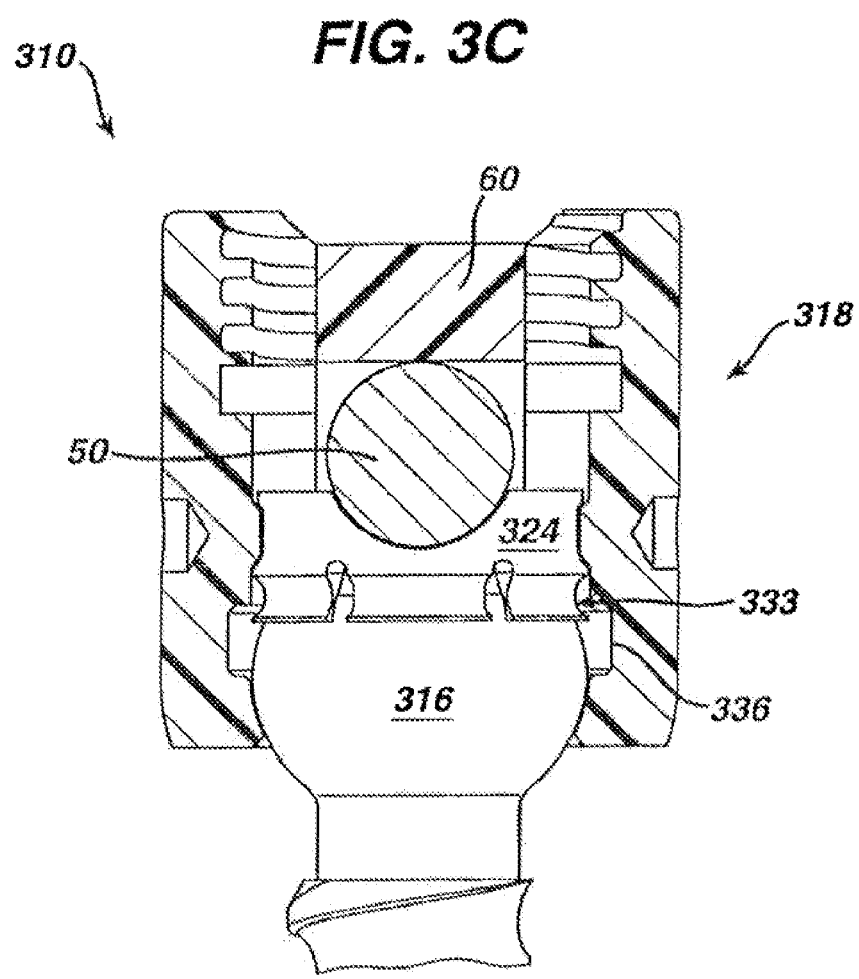
FIG. 3C illustrates the polyaxial bone screw assembly of FIG. 3B with a rod and closure mechanism disposed therein.

FIGS. 3A-3C illustrate another embodiment of a polyaxial bone screw assembly 310 that includes an engagement feature that is effective to maintain the angular orientation of a bone screw 312 with respect to a receiver member 318. In this embodiment, rather than providing a separate engagement member, such as snap ring 234 shown in FIGS. 2A-2C, the compression cap 324 is modified to include an expandable portion that is adapted to fit around and frictionally engage the spherical head 316 of the bone screw 312. While the expandable portion can have virtually any configuration, in an exemplary embodiment the distal end 324b of the compression cap 324 includes a collet 333 formed therearound having several spaced apart finger-like members 334 that are separated by slots 335 which allow the finger-like members 334 to expand. The collet 333 can include any number of finger-like members 334 that can be spaced apart at varying distances. Once the cap is retained in place within the receiver member, the fingers 334 will bear upon the spherical head 316 of the screw 312. This can be achieved by deforming the fingers 334 on the cap inward prior to assembly, so that they contact the spherical head 316 of the screw 312 once inserted. Alternatively, the concave underside of the cap 324 can be machined so that the radius is smaller than a radius r of the spherical head 316 of the screw 312. This interference will also cause the fingers 334 to bear upon the head 316 of the screw 312. In use, as the compression cap 324 is moved distally on to the head 316, the collet 333 is forced to expand around the spherical head 316 of the bone screw 312 to engage the head and create the friction necessary to maintain the angular orientation of the screw 312 with respect to the receiver 318, as shown in FIG. 3B. As previously indicated, the compression cap 324 can be retained in this position by deforming the material 332a, 332b in the receiver member 318 into the corresponding detents 330a, 330b in the compression cap 324.

Still referring to FIG. 3B, in a further embodiment, the receiver member 318 can include an annular groove 336 formed therein for receiving the expandable fingers 334 of the collet 333. The groove 336, which is similar to groove 236 shown in FIG. 2A, prevents the collet 333 from interfering with the locking function of the compression cap 324. In other words, when a rod 50 is seated within the rod-receiving recess 326 formed in the compression cap 324, and a closure mechanism 60 is applied to lock the rod 50 within the receiver member 318, as shown in FIG. 3C, the compression cap 324 locks the position of spherical head 316 within the receiver member 318. The groove 336 thus receives the collet 333 to prevent the collet 333 from interfering with the locking forces created between the compression cap 324 and the spherical head 316.

Figure 4A:
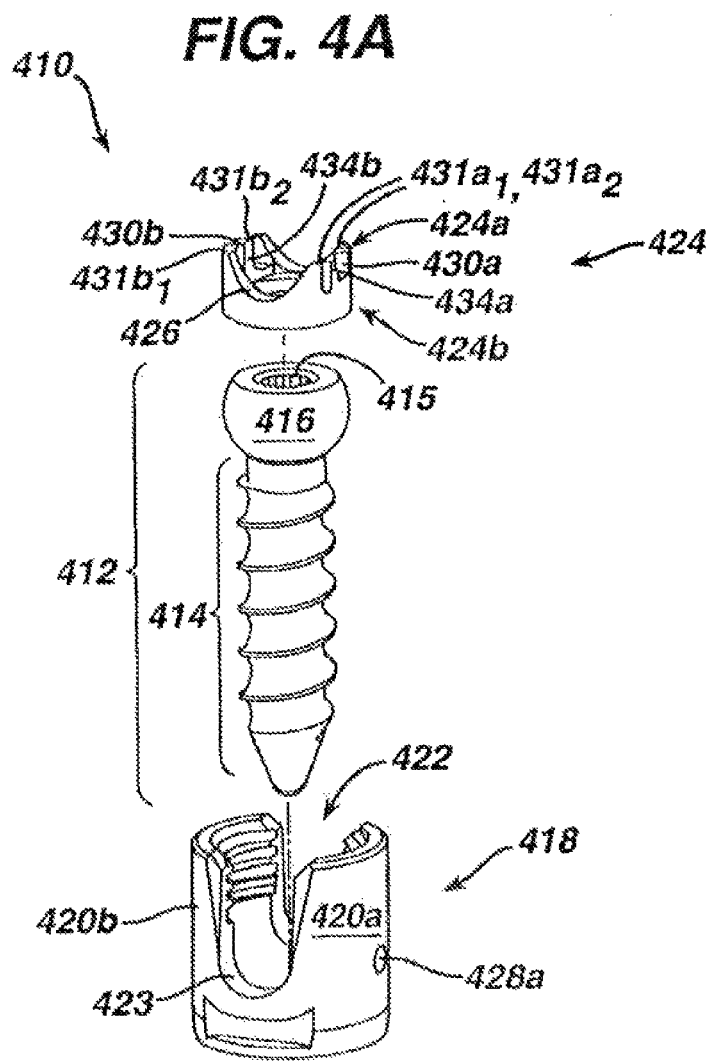
FIG. 4A is a perspective view of another embodiment of a polyaxial bone screw assembly, in the disassembled state, having a compression cap with a leaf-spring for engaging the head of a bone screw in accordance with the present invention.
Figure 4B:
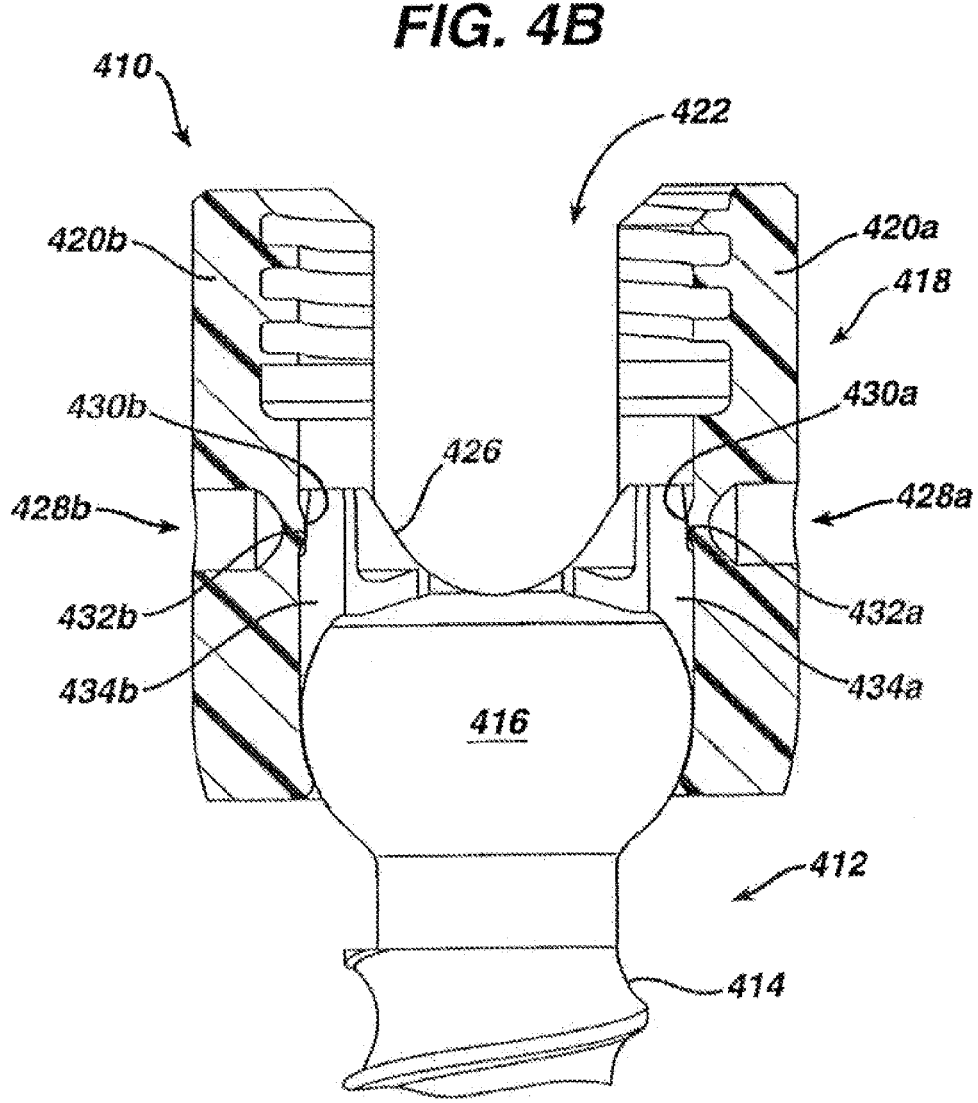
FIG. 4B is an enlarged, cross-sectional view of the a portion of the polyaxial bone screw assembly shown in FIG. 4A.

FIGS. 4A-4B illustrate yet another embodiment of a polyaxial bone screw assembly 410 in which a leaf-spring compression cap 424 is used to engage the spherical head 416 of the bone screw 412 to create the frictional forces necessary to maintain the angular orientation of the bone screw 412 with respect to a receiver member 418. As shown in FIG. 4A, the compression cap 424 includes a first pair of slots $431a_1$, $431a_2$ formed on opposed sides of the first detent 430a, and a second pair of slots $431b_1$, $431b_2$ formed on opposed sides of the second detent 430b. Each pair of slots $431a_1$, $431a_2$, $431b_1$, $431b_2$ extends from a proximal end 424a of the compression cap 424 toward the distal end 424b, terminating just proximal to the distal end 424b. As a result, the slots $431a_1$, $431a_2$, $431b_1$, $431b_2$ form sidewall portions 434a, 434b therebetween that are flexible, thereby forming a leaf spring. In use, as shown in FIG. 4B, when the deformable material 432a, 432b in the receiver member 418 is deformed into the corresponding detents 430a, 430b in the compression cap 424, the sidewall portions 434a, 434b flex inward thereby contracting around, and preferably creating a downward pressure on, the spherical head 416 of the bone screw 412. As a result, friction is created between the compression cap 424 and the spherical head 416 to maintain the angular orientation of the screw 412 with respect to the receiver member 418. A person skilled in the art will appreciate that a variety of other techniques can be used to create a spring-like compression cap 424 that is effective to engage the spherical head 416 of the screw 412.

Figure 5B:
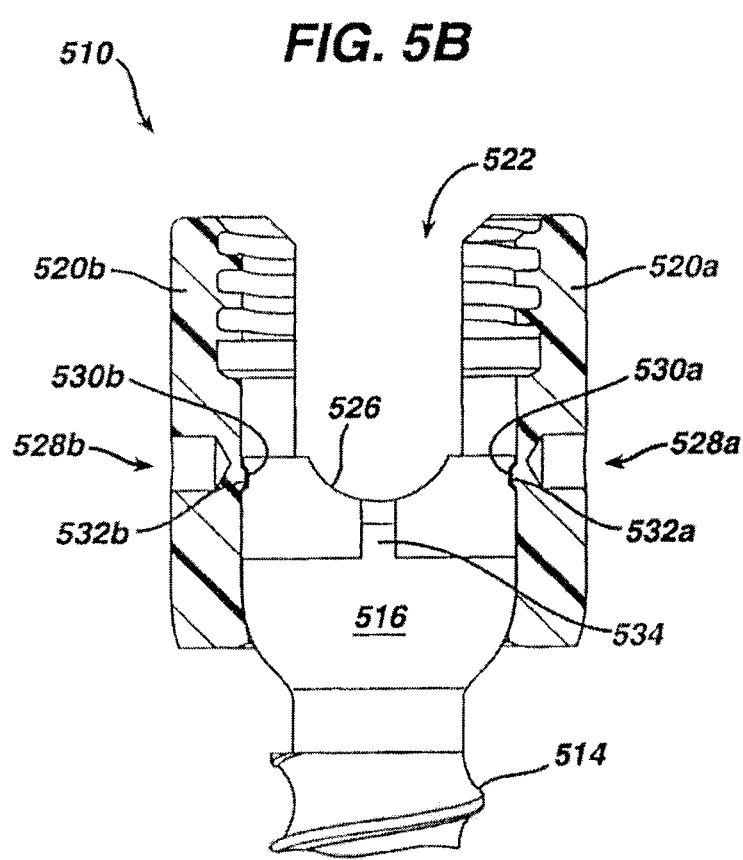
FIG. 5B is an enlarged, partially cross-sectional view of a portion of the polyaxial bone screw shown in FIG. 5A.

FIGS. 5A-5B illustrate yet another embodiment of a polyaxial bone screw assembly 510. In this embodiment, the compression cap 524 includes an axial slot 534 formed therein to allow the compression cap 524 to be contracted to engage the spherical head 516 of the bone screw 512. While the slot 534 can be formed anywhere in the compression cap 524, the slot 534 is preferably formed in the portion of the sidewall that extends between the opposed detents 530a, 530b, and more preferably the slot 534 is equidistant from each detent 530a, 530b to allow the compression cap 524 to be swaged evenly in a distal direction. FIG. 5B illustrates the compression cap 524 in the contracted state around the head 516 of the bone screw. The deformable material 532a, 532b in the receiver member 518 is deformed into the detents 530a, 530b in the compression cap 524 to contract the compression cap 524 around the spherical head 516. As a result, the frictional forces created by the compression cap 524 radially contracting around the spherical head 516 are effective to allow the bone screw 512 to be maintained at a desired angular orientation with respect to the receiver member 518.

A person skilled in the art will appreciate that a variety of other techniques can be used to apply friction to the spherical head of a polyaxial bone screw to allow the bone screw to be maintained in a desired angular orientation before locking the bone screw within the receiver member. By way of non-limiting example, the spherical head of the polyaxial screw can include a coating or surface treatment thereon to hinder movement of the screw head with respect to the receiver member. Alternatively, or in addition, the spherical head, the compression cap, and/or the receiver member can include one or more protrusions formed thereon to frictionally engage the spherical head to allow the orientation of the head to be maintained in a desired configuration. The protrusions can be, for example, formed from a plastic material that is effective to interfere with the free rotational movement of the screw within the receiver.

A person skilled in the art will appreciate that this design is applicable to other polyaxial fixation devices, including other screws, cross-connectors, hooks, bolts, etc., and it is not intended to be limited to use with a polyaxial bone screw. A person skilled in the art will also appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A polyaxial fixation device, comprising:
   a receiver member having
      opposed arms that define a rod-receiving recess therebetween,
      a recess formed in a distal end thereof, and
      an annular groove formed in an internal surface thereof;
   a bone screw having a head seated within the recess in the receiver member, and a shank extending through an opening formed in a distal end of the receiver member and configured to engage bone; and
   an engagement member disposed within the receiver member at a location substantially proximal to the head of the bone screw, the engagement member being expandable into the groove, and the engagement member being effective to engage the head of the bone screw to provide sufficient friction between the head and the receiver member to enable the receiver member to be maintained in a desired angular orientation relative to the shank before locking the head within the receiver member.

2. The device of claim 1, wherein the engagement member has at least, one slot formed therein and configured to allow the engagement member to be contracted to provide sufficient friction between the head and the receiver member to enable the receiver member to be maintained in a desired angular orientation relative to the shank before locking the head within the receiver member.

3. The device of claim 1, wherein the engagement member includes a concave distal surface configured to seat at least a portion of the head of the bone screw.

4. The device of claim 1, wherein the engagement member is mated to the receiver member such that proximal movement of the engagement member is prevented.

5. The device of claim 1, wherein at least a portion of the engagement member has a diameter that is expandable or deformable to frictionally engage the spherical head.

6. A method for implanting a polyaxial fixation device, comprising:
   implanting a threaded shank in bone, the shank having a head formed on a proximal end thereof and seated within a cavity in a receiver member such that the receiver member is polyaxially movable relative to the head, the receiver member including an engagement member located substantially proximal to the head, the engagement member being expandable into a groove formed within the receiver member, and the engagement member engaging the head to provide sufficient friction between the head and the receiver member to maintain the receiver member in a desired angular orientation relative to the shank before locking the head within the receiver member.

7. The method of claim 6, further comprising applying a locking element to the receiver member to lock the receiver member in a fixed position relative to the shank.

8. The method of claim 6, further comprising positioning a spinal fixation rod within the receiver member, and applying a locking element to the receiver member to lock the spinal fixation rod within the receiver and to lock the receiver member in a fixed position relative to the shank.

9. The method of claim 6, wherein the receiver member includes opposed side bores formed therein and having a deformable material extending thereacross, the deformable material being swaged inward into opposed detents in the engagement member to retain the engagement member within the receiver member.

* * * * *